United States Patent [19]
Pai

[11] Patent Number: 5,842,245
[45] Date of Patent: Dec. 1, 1998

[54] ELECTRIC TOOTHBRUSH ASSEMBLY

[76] Inventor: Chung-Jen Pai, No. 10, Lane 423, Ching Shin St., Chung Ho, Taipei Hsien, Taiwan

[21] Appl. No.: 83,755
[22] Filed: May 26, 1998
[51] Int. Cl.⁶ .................................................... A61C 17/22
[52] U.S. Cl. ............................................................. 15/22.1
[58] Field of Search ................................. 15/22.1, 28, 29

[56] References Cited

U.S. PATENT DOCUMENTS 5,778,474  7/1998  Shek .......................................... 15/22.1

FOREIGN PATENT DOCUMENTS 537465   4/1993   European Pat. Off. ................. 15/22.1
1166163  11/1958  France ..................................... 15/22.1

*Primary Examiner*—Mark Spisich
*Attorney, Agent, or Firm*—Bacon & Thomas

[57] ABSTRACT

An improved electric toothbrush assembly including a handle and a brush portion. The handle has an output shaft which is provided with a vertical positioning rod. The brush portion includes a brushing housing, a brush cover, a brush rod received between the brush housing and brush cover, and two brush heads. The brush housing is coupled to the handle as well as the brush cover. The housing is provided with a brush face formed with two parallel elongated face slots. The brush cover is provided with a cover pin projecting from a middle section thereof. The brush rod has hooks at a bottom side thereof, a vertical elongated slot near a middle section thereof and two grooves at an upper side thereof corresponding to the brush face of the brush housing. The brush heads are each provided with brush axles received therein which pass through the grooves of the brush rod and the face slots of the brush housing. The hooks of the brush rod engage the positioning rod of the handle. The cover pin passes through the slot of the brush rod. When the output shaft of the handle performs linear movement, it will bring the brush rod to reciprocate in a linear direction while the brush heads displace inwardly and outwardly respectively in relation to the brush face when the brush axles move along the grooves of the brush rod.

5 Claims, 3 Drawing Sheets

ELECTRIC TOOTHBRUSH ASSEMBLY

BACKGROUND OF THE INVENTION (a) Field of the Invention

The present invention relates to an improved toothbrush assembly, and more particularly to a toothbrush assembly in which brush heads respectively displace inwardly and outwardly when a brush rod is brought by an output shaft to reciprocate in a linear direction.

(b) Description of the Prior Art

A conventional electric toothbrush operates by means of a direct current motor output which translates rotation of the motor into a reciprocating movement to drive a brush head that, due to the reciprocating movement, rotates to brush the teeth of the user. An example of such toothbrushes is disclosed in U.S. Pat. No. 5,727,273 for "Electric Toothbrush Assembly with Sterilizing and Charging device" to the inventor of the present invention.

It has been found that brushing should be done in an up-and-down direction, not left-and-right, and the rotation of the brush head is not proper for up-and-down brushing. Improvement on the prior art is therefore necessary.

SUMMARY OF THE INVENTION

A primary object of the present invention is to provide an improved toothbrush assembly in which two brush heads displace inwardly and outwardly respectively when a brush rod is driven by an output shaft to reciprocate in a linear direction, thus eliminating the drawback with the prior art and ensuring oral hygiene.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
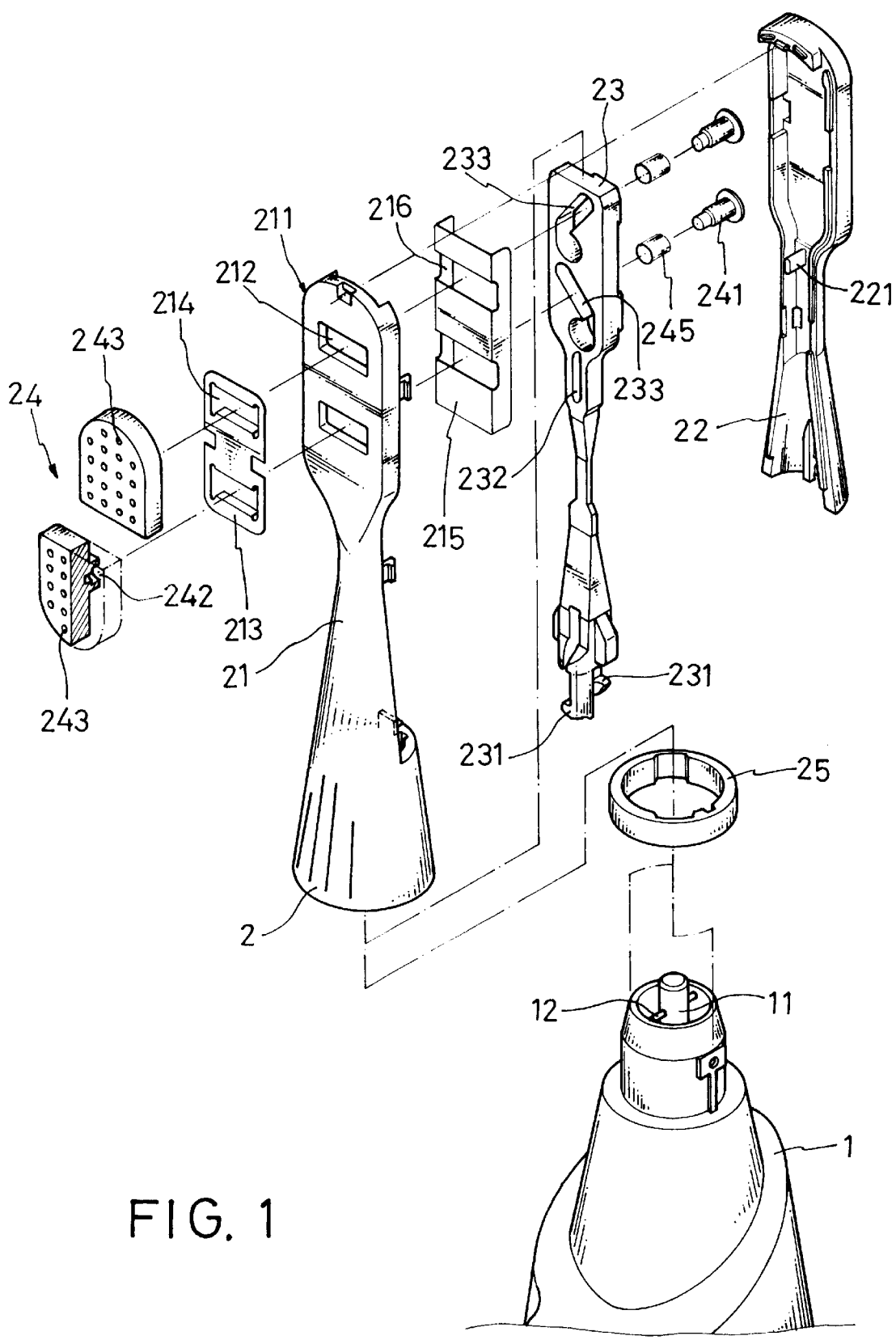
FIG. 1 is a perspective exploded view of the electric toothbrush assembly of the present invention.

Referring to the drawings, the improved electric toothbrush assembly according to the present invention essentially comprises a handle 1, and a brush portion 2.

The handle 1 has an interior accommodating therein a battery, a motor, and a transmission device which causes a distal output shaft to perform linear up-and-down movements. As such a structure is well known in the art, e.g., the above-mentioned U.S. Pat. No. 5,727,273, it will not be discussed in detail herein. The difference between the handle 1 of the present invention and that of the prior art is that a position rod 12 is vertically insertably provided on an output shaft 11 projecting from an uppermost part of the handle 1 for connecting the brush portion 2 for operation purposes.

The improvement provided by the present invention resides in the brush portion 2. As shown, the brush portion 2 includes a brush housing 21, a brush cover, and a brush rod 23 sandwiched between the brush housing 21 and the brush cover, two brush heads 24, and a coupling ring 25.

The brush housing 21 has a cylindrical portion at a lower side which is sized to match the coupling ring 25 and has a bottom edge that may be recessed or projecting for purposes of engagement with the handle 1. The brush housing 21 is also provided with engagement means such as pins and grooves at an upper side and lateral sides thereof adapted for coupling with the brush cover 22. In addition, the brush housing 21 includes a brush face 211 at the upper side, the brush face 211 is provided with two parallel elongated face slots 212 for passage of brush axles 241 of the brush heads 24. At the same time, in order that friction or wear between the brush face 211 and the brush head 24 may be reduced or slowed down, a face cover 213 having two parallel elongated holes 214 corresponding to the face slots 212 of the brush face 211 is fitted to a front side of the brush face 211. The opposite side of the brush face 211 also has a back cover 215 having two parallel elongated holes 216 corresponding to the face slots 212 and the elongated holes 214 fitted thereto to reduce wear.

The size and shape of the brush cover 22 match those of the brush housing 21 so that they may be coupled together. The brush cover 22 includes a cover pin 221 extending horizontally from a middle section thereof to serve as a pivot during up-and-down movement of the brush rod 23. Like the brush housing 21, the brush cover 22 is provided with engagement means such as pins and grooves at its peripheries for coupling with the brush housing 21.

The brush rod 23 is a flat elongated structure so that it may be sandwiched between the brush housing 21 and the brush cover 22. It includes two hooks 231 at both sides of a bottom side thereof respectively for engaging the positioning rod 12 of the handle 1. The hooks 231 are oppositely oriented and preferably have an oblique angle to enhance the firmness of the engagement. The brush rod 23 further includes a vertical elongated slot 232 at the center near its upper side. The size of the slot 232 is slightly greater than that of the cover pin 221. The upper side of the brush rod 23 corresponding to the brush face 211 is provided with two hollowed out grooves 233 that are obliquely arranged and oriented in different directions for passage of the brush axles 241 of the brush heads 24.

The brush heads 24 are each a substantially square structure with curved outer edges. The two brush axles 241 are secured in respective insert holes 242 of the brush heads 24. In addition, an outer side of each brush head 24 is provided with a plurality of non-through holes 243 in which bundles of bristles 244 (see FIG. 2) may be planted in position. Furthermore, in order to resist wear, the brush axles 241 may be fitted with respective sleeves 245.

The coupling ring 25 is sized to match the upper edge of the handle 1 and the bottom portion of the brush housing 21 so that it may be coupled thereto. And to ensure water tightness, the coupling ring 25 is coupled thereto by supersonic waves. The coupling ring 25 is actually optionally. The handle 1 and the brush housing 21 may be configured to have a longer length and are directly coupled using supersonic waves.

Figure 2:
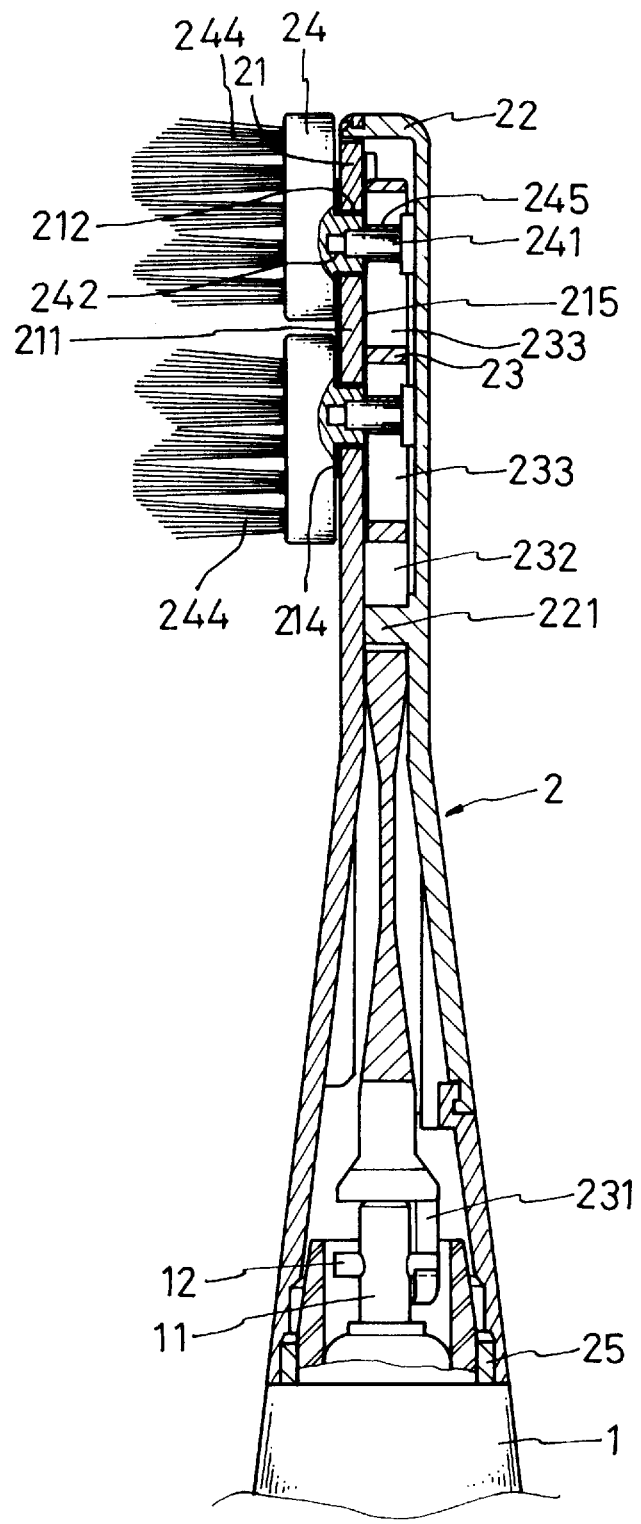
FIG. 2 is a side sectional assembled view of the present invention.

Referring to FIG. 2, in assembly, the brush rod 23 is received in the space between the brush housing 21 and the brush cover 22, with the brush axles 241 passing through the grooves 233 to couple to the brush head 24. The hooks 231 of the brush rod 23 are fastened to the positioning rod 12 of the output shaft 11 of the handle 1 such that the brush head 24 and the bristles 244 thereon are exposed on the outside.

Figure 3:
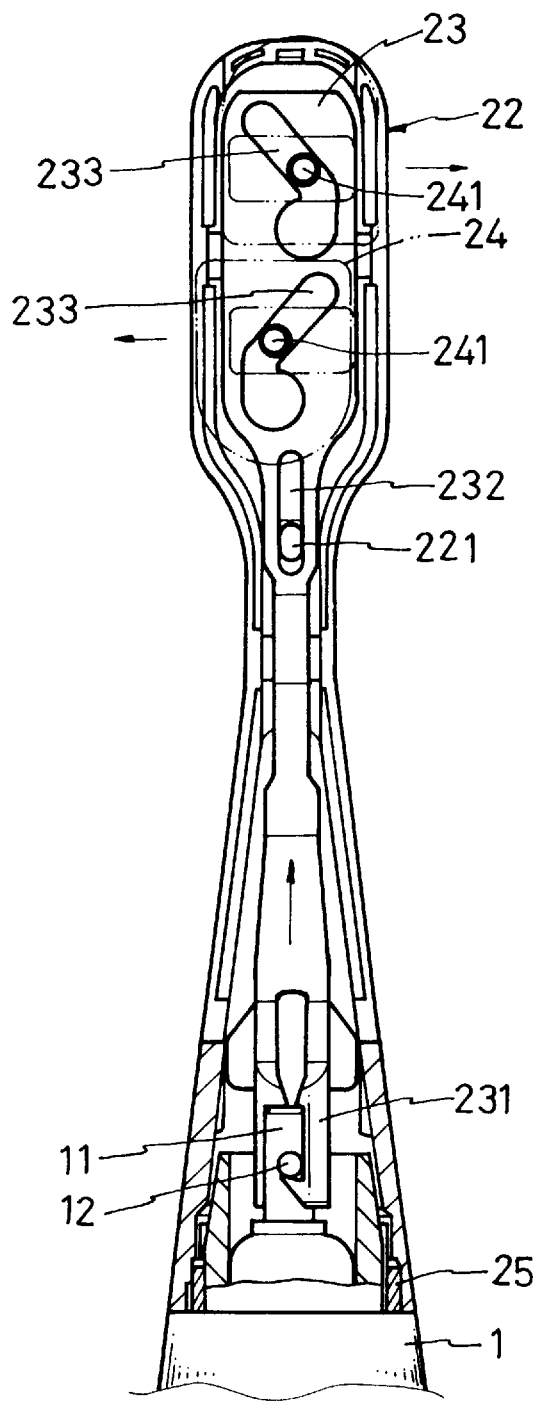
FIG. 3 is a front sectional view of the present invention in which a brush rod is located at a highest position.
Figure 4:
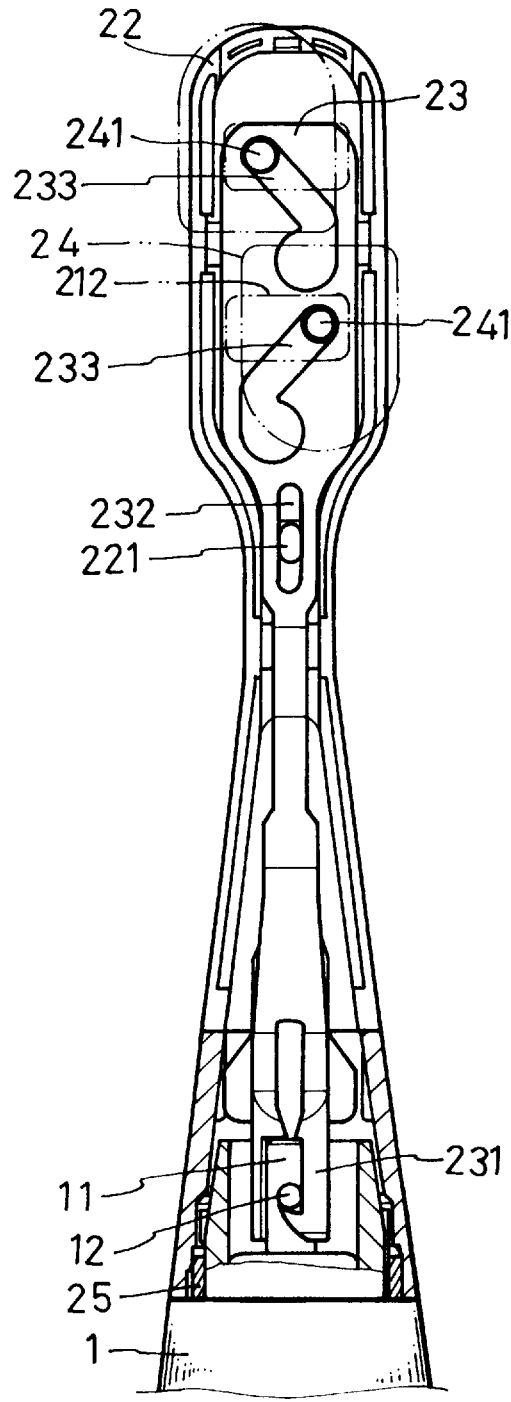
FIG. 4 is a front sectional view of the present invention in which brush head portions move outwardly when the brush rod displaces downwardly.

Referring to FIGS. 3 and 4, the brush portion 2 and the handle 1 are firstly coupled. If the output shaft 11 is located at a low position, it shows that the positioning rod 12 is not yet connected to the brush rod 23. At this point, by turning on the power of the handle 1 to cause the output shaft 11 to displace up and down, the positioning rod 12 will, during the process of displacement of the output shaft, move along the inclination of the hooks 231 to engage with the hooks 231, synchronously bringing the brush rod 23 to displace up and down. Therefore, when the brush rod 23 is at a highest point as shown in FIG. 3, the two brush axles 241 will be at lowest points of the respective grooves 233. And at this time, the two brush heads 24 are roughly located on the brush face 211. But when the brush rod 23 displaces downwardly, the brush axles 241 move along the grooves 233 to slidably displace upwardly and outwardly so that the brush heads 24 also slidably displace outwardly. In this way, the electric toothbrush of the present invention performs horizontal brushing movements, the brush heads 24 will respectively move upwardly and downwardly at a high speed. This is healthy brushing meeting the requirements of oral hygiene.

Compared to the prior art, the present invention enabling the bristles to move both upwardly and downwardly during brushing provides a vast improvement.

Although the present invention has been illustrated and described with reference to the preferred embodiment thereof, it should be understood that it is in no way limited to the details of such embodiment but is capable of numerous modifications within the scope of the appended claims.

What is claimed is:

1. An improved electric toothbrush assembly, comprising:

a handle having an interior accommodating therein power and transmission means, a distal output shaft performing linear up-and-down movements, and an output shaft projecting from an upper side of said handle and having a positioning rod vertically insertably provided thereon;

a brush portion, including a brush housing, a brush cover, a brush rod sandwiched between said brush housing and said brush cover, and two brush heads, wherein said brush housing includes a cylindrical portion at a lower side thereof of a size corresponding to an upper edge of said handle, and fastening means at an upper side thereof and lateral sides for coupling with said brush cover; said brush housing being provided with a brush face at the upper side, said brush face being formed with two parallel elongated face slots;

said brush cover is sized and shaped to match said brush housing and has corresponding fastening means for coupling with said brush housing, said brush cover being provided with a cover pin projecting horizontally from a middle section thereof;

said brush rod is an elongated structure having hooks at both sides of a bottom side thereof respectively, a vertical elongated slot near a middle section thereof of a size slightly greater than that of said cover pin, and two hollowed out grooves arranged obliquely and oriented in different directions at an upper side thereof corresponding to said brush face of said brush housing; and said brush heads are each provided with an insert hole at that side thereof facing said brush housing, and a plurality of non-through holes at an opposite side for planting of bristles, said brush heads further including respective brush axles for insertion into said insert holes;

whereby said brush axles pass through said grooves of said brush rod and said face slots of said brush housing to project from said brush housing and couple to said brush heads; said hooks of said brush rod engage said positioning rod of said handle; said cover pin passes through said slot of said brush rod; said brush cover is fitted with said brush housing; and said brush portion is connected to said handle, when said output shaft of said handle performs linear movement, it will bring said brush rod to reciprocate in a linear direction while the brush heads will displace inwardly and outwardly respectively in relation to said brush face when said brush axles move along said grooves of said brush rod.

2. The improved electric toothbrush assembly as defined in claim 1, further comprising a face cover fitted to a front side of said brush housing and a back cover fitted to a back side of said brush housing, said face cover and said back cover being both provided with parallel elongated holes corresponding to said face slots.

3. The improved electric toothbrush assembly as defined in claim 1, wherein said brush axles are each fitted with respective sleeves to resist wear.

4. The improved electric toothbrush assembly as defined in claim 1, wherein a coupling ring is disposed between a bottom portion of said brush housing and a top portion of said handle, the bottom portion of said brush housing and the top portion of said handle being reduced in length.

5. The improved electric toothbrush assembly as defined in claim 1, wherein said hooks of said brush rod are slightly oblique to enhance the firmness of their engagement with said positioning rod.

* * * * *